United States Patent [19]

Nigra

[11] Patent Number: 6,028,105
[45] Date of Patent: Feb. 22, 2000

[54] TOPICAL DRUG DELIVERY COMPOSITION AND METHOD

[76] Inventor: Thomas P. Nigra, Rte. 4, Box 509, Easton, Md. 21201

[21] Appl. No.: 08/484,548

[22] Filed: Jun. 7, 1995

Related U.S. Application Data

[63] Continuation of application No. 08/199,989, Feb. 22, 1994, abandoned, which is a continuation of application No. 07/944,020, Sep. 11, 1992, abandoned, which is a continuation of application No. 07/677,375, Mar. 27, 1991, abandoned, which is a continuation of application No. 07/334,511, Apr. 6, 1989.

[51] Int. Cl.$^7$ ............................. A01N 37/00; A01N 31/14
[52] U.S. Cl. ............................................ 514/560; 514/723
[58] Field of Search ...................... 514/560, 723

[56] References Cited

U.S. PATENT DOCUMENTS

| | | | |
|---|---|---|---|
| 2,420,519 | 5/1947 | Brown | 260/345 |
| 3,699,230 | 10/1972 | Beauchamp, Jr. et al. | 424/272 |
| 3,729,568 | 4/1973 | Kligman | 514/419 |
| 3,906,108 | 9/1975 | Felty | 426/318 |
| 3,989,816 | 11/1976 | Rajadhyaksh | 424/88 |
| 4,247,547 | 1/1981 | Marks | 424/381 |
| 4,299,826 | 11/1981 | Luedders | 424/181 |
| 4,316,893 | 2/1982 | Rajadhyaksha | 426/180 |
| 4,322,359 | 3/1982 | Hillard et al. | 260/347.8 |
| 4,405,616 | 9/1983 | Rajadhyaksha | 424/244 |
| 4,508,634 | 4/1985 | Elepano et al. | 252/163 |
| 4,603,616 | 8/1986 | Kligman | 514/549 |
| 4,888,342 | 12/1989 | Kligman | 514/419 |
| 4,923,900 | 5/1990 | De Villez | 514/714 |

OTHER PUBLICATIONS

Weiss, J.S., et al., "Topical Tretinoin Improves Photoaged Skin: A Double–Blind Vehicle–Controlled Study," *Journal of the American Medical Association*, vol. 259, Jan. 22/29, 1988, pp. 527–532.

Weiss, R., "Wrestling with Wrinkles," *Science News*, vol. 134, Sep. 24, 1988, pp. 200–202.

Merdi Index, 10$^{th}$ Ed 1985, Abstract 7756.

A.B. Barua and J.A. Olson, Percutaneous Absorption, Excretion and Metabolism of All–trans–Retinoyl B–Glucuronide and of All trans–Retinoic Acid in the Rat, 1996 Skin Pharmacol; 9: 17–26

Commonwealth of Virginia Pharmacy Act, p. 34, Jul. 1, 1993.

McCutcheon's Detergents & Emulsifiers, 1971 Amnd., p. 24.

*Primary Examiner*—Russell Travers
*Attorney, Agent, or Firm*—Maryellen Feehery; William J. McNichol, Jr.

[57] ABSTRACT

A topical composition for delivering an effective amount of a pharmaceutically acceptable drug, including laureth-4, propylene glycol, dimethylsorbide, and a pharmaceutically acceptable diluent is described as an improved drug delivery composition. Further, a method of transepithelial delivery of a drug to a human by topical application to the skin of a human of a composition including laureth-4, propylene glycol, dimethylsorbide, a pharmaceutically acceptable diluent of water and ethanol and an effective amount of a pharmaceutically acceptable drug has beneficial delivery effects.

9 Claims, No Drawings

TOPICAL DRUG DELIVERY COMPOSITION AND METHOD

This is a continuation of application Ser. No. 08/199,989, filed Feb. 22, 1994, which is a continuation of application Ser. No. 07/944,020, filed Sep. 11, 1992, which is a continuation of application Ser. No. 07/677,375, filed Mar. 27, 1991, which is a continuation of application Ser. No. 07/334, 511, filed Apr. 6, 1989, all abandoned.

TECHNICAL FIELD

The present invention relates, in general, to a drug delivery composition and method, and, in particular, to a drug delivery composition and method for topical delivery of drugs, such as retinoids, which must be applied diligently and consistently to achieve optimal and reliable drug efficacy.

BACKGROUND OF THE INVENTION

It is to be understood that the citation of art contained herein is in no way to be construed as an admission that said art is suitable reference against the present patent application nor should this citation act as a waiver of any rights to overcome said art which may be available to the applicant.

The topical application of many active agents is desirable to achieve effective concentrations of the agents at the target site. From a practical standpoint, however, skin preparations are often not applied conscientiously by the user for a variety of reasons, and thus the optimal results are frequently not achieved. Lack of user acceptance often results from the oiliness, tackiness, excessive film formation, odor, etc. that accompany many topical preparations. In addition, repeated exposure to certain topical delivery systems results in irritation or drying of the skin.

The continuous, i.e., daily, long-term, month-to-month, and consistent topical application of at least one specific agent has recently been reported to result in a reversal of photoaging of the skin. The agent, tretinoin (all trans-retinoic acid) was earlier reported to be beneficial in the treatment of acne, seborrhea and psoriasis. Most recently Weiss and his co-workers have reported that tretinoin can improve the effects of photoaging including wrinkling, sallowness, roughness and mottled pigmentation characteristic of photoaged skin when applied as a 0.1% cream daily for sixteen weeks. Weiss, J. S., et al., Topical Tretinoin Improves Photoaged Skin: A Double-blind Vehicle-Controlled Study, JAMA, 259:527–532, 1988. Similarly, Voorhees and co-workers have reported further and extended beneficial results may be achieved from the consistent and continuous application of the 0.1% cream for a period in excess of fourteen months. FDC Reports, Vol. 9, No. 50, Dec. 12, 1988; Weiss, J. S., et al., Topical Tretinoin in the Treatment of Aging Skin, J. Am. Acad. Dermatol., 19:169–175, 1988. However, these researchers reported that most patients experience dermatitis as a result of treatment with the tretinoin cream. The initial dermatitis, which is associated with xerosis, peeling Rand subjective irritation, lasts from two weeks to three months while a second inflammatory phase, presumably of subclinical actinic keratosis, is experienced by some patients in which the erythema is more punctate or reticulate.

While the dermatitis reported by Weiss et al. and Voorhes appears to result from the tretinoin itself, the results underscore the need for a vehicle which enhances the absorption of the active agent so that the desired end result can be achieved using a dose of the agent less likely to cause irritation, as well as a vehicle which is favorably accepted by the user so as to encourage and assure consistent, diligent and continuous use as directed.

Most topical drugs are administered on an outpatient basis. Thus, it is required that the patient apply the drug several times daily for the drug to have its optimal effect. Because the drug is topically applied, it must be administered periodically due to washing or wearing off. Most prior art delivery systems for topical drugs are not as pleasant as they could be to the patient, in that the delivery vehicle itself, or its effect upon the skin, is shiny, oily, tacky, drying, constricting, sweaty, greasy or malodorous. Because the drug delivery system is not pleasant, patients tend to stop using the drug, or do not use it according to the proper schedule. When the drug is not applied in the optimal manner, because of the unpleasant delivery system, then the condition for which the drug is applied is not optimally treated.

Thus, there is a need for a topical delivery system for drugs and other active agents that will encourage the consistent and continuous application needed to achieve optimal and reliable efficacy, and that can be comfortably used to deliver materials to the skin surface for the purpose of providing epidermal, dermal and/or subcutaneous benefits.

SUMMARY OF THE INVENTION

The drug topical drug delivery composition and method of the present invention provides a method and composition that promotes a high degree of patient compliance in encouraging their conscientious daily application of active agents over months and years which produces more reliable and assured therapeutic results.

The topical drug delivery composition and method of the present invention also provides a new composition for delivering drugs and other active agents that has several desirable advantages in delivering materials to the skin surface for the purpose of providing epidermal, dermal, subcutaneous and system benefits.

The composition and method of the present invention permits the delivery vehicle to be imperceptible and invisible after application, thus eliminating the initial and residual oiliness, greasiness, tackiness, odor, color, shine and subjective annoyances and irritations of prior art vehicles.

The topical drug delivery composition of the present invention also permits the skin of the patient to become softened and smoothed rather than suffer from clinical problems often associated with other prior art topical delivery vehicles, such as dry, cracked, red, irritated skin.

The composition of the present invention also permits the efficient and continuous release of active agents onto the surface of the skin and may enhance penetration into the epidermis and underlying dermal and subcutaneous tissues.

Thus, the present invention relates in general to a drug delivery composition comprising: i) an effective amount of a pharmaceutically acceptable surface tension reducing agent; ii) an effective amount of a pharmaceutically acceptable skin hydrating agent; and iii) an effective amount of a hydrophilic-lipophilic coupling agent. In addition, the present invention may optionally contain a pharmaceutically acceptable diluent or carrier.

In another embodiment, the present invention relates to a topical preparation comprising the above-described delivery composition and an amount of a pharmaceutically acceptable retinoid sufficient to reverse the effects of aging such as wrinkling of skin.

The present invention further relates to a method of topically delivering a drug to the skin of an animal or human comprising the steps of:

a) preparing a topical delivery composition comprising:
  i) an effective amount of one or more pharmaceutically acceptable surface tension reducing agents;
  ii) an effective amount of one or more pharmaceutically acceptable skin hydrating agents;
  iii) an effective amount of one or more hydrophilic-lipophilic coupling agents; and
  iv) an effective amount of a pharmaceutically acceptable drug; and b) applying the topical delivery composition to the skin of the animal or human.

The topical delivery composition of the method of the present invention provides a means with which to deliver a pharmacologically effective amount of one or more active ingredients. Furthermore, the topical delivery composition can contain an additional pharmaceutically acceptable carrier or diluent.

Accordingly, it is an object of the present invention to provide a topical drug delivery composition that promotes patient compliance by encouraging continuous and conscientious application of active ingredients on a schedule as directed, thus producing more reliable and assured therapeutic results.

It is a specific object of the present invention to provide a topical drug delivery composition wherein the vehicle is imperceptible and essentially invisible after application, thus eliminating initial and residual oiliness, greasiness, excessive film formation, tackiness, odor and shine.

It is another object of the present invention to provide a topical drug delivery composition that softens and soothes the skin and reduces clinical problems often associated with topical delivery vehicles, such as dry, cracked, red, irritated skin without becoming aesthetically less desirable to the person using the formula.

It is another object of the present invention to provide a method of effecting the efficient and continuous release of active ingredients into and within the surface of the skin and, where desirable, further penetration into the epidermis, and into the underlying dermal and subcutaneous tissues.

It is another object of the present invention to provide pharmaceutical compositions suitable for topical delivery of retinoids which significantly reduce the art-recognized problems associated with retinoid-containing compositions.

These and other objects, features and advantages of the present invention will become apparent after a review of the following detailed description of the disclosed embodiments and the appended claims.

DETAILED DESCRIPTION OF THE INVENTION

Thus, the present invention relates to a drug delivery composition comprising: i) an effective amount of a pharmaceutically acceptable surface tension reducing agent; ii) an effective amount of a pharmaceutically acceptable skin hydrating agent; and iii) an effective amount of a hydrophilic-lipophilic coupling agent. In addition, the present invention may optionally contain a pharmaceutically acceptable diluent or carrier.

The components of the topical drug delivery composition are preferably colorless, clear or nondeleteriously tinted or colored and nonmalodorous, however, the final preparation may be colored, tinted or clear, as well as being scented or unscented as desired. Such aspects as color and scent of the final product can be selected such that the product's aesthetic appeal is enhanced. The invention further relates to topical preparations containing an active agent in association with such a delivery composition.

The surface tension reducing agents of the invention include anionic, nonionic, cationic and amphoteric surfactants known in the art that are, when incorporated into the vehicle and applied to the skin, essentially clear, colorless and non-malodorous, and that are dermatologically safe and compatible with the active agents as well as the other vehicle ingredients. The surface tension reducing agents can be used singly or in combination in a concentration ranging from approximately 0.001 to 5.0% w/v, advantageously, in the range of approximately about 0.05 to 1.5%. Suitable surface tension reducing agents include, but are not limited to, laureth-4, octoxynol-9, cocoamphocarboxyglycinate, dioctyl sodium sulfosuccinate and benzethonium chloride.

The skin softening agents of the invention include such agents known in the art that are, when incorporated into the vehicle and applied to the skin, essentially clear, colorless, non-malodorous, and that are dermatologically safe and are compatible with the active agents as well as the other vehicle ingredients. The skin softening agents can be used singly or in combination in a concentration ranging from approximately 0.01 to 10.0% w/v, advantageously, in the range of from approximately 0.05 to 5.0%. Skin softening agents suitable for use in the present invention include, by are not limited to, glycerin, propylene glycol, caprylic/capric triglyceride, pantothenol and its derivatives and related moieties, and hyaluronic acid and related moieties.

The hydrophilic-lipophilic coupling agents of the invention include such agents known in the art that are when incorporated into the vehicle and applied to the skin essentially clear, colorless, non-malodorous, and that are dermatologically safe and compatible with the active, and other vehicle, ingredients. The hydrophilic-lipophilic coupling agents can be used singly or in combination in concentrations ranging from approximately 0.01 to 5.0% w/v, advantageously, in the range of approximately 0.05 to 2.5%. Hydrophilic-lipophilic coupling agents include, but are not limited to, dimethylisosorbide, diisopropyl adipate, dioctyl maleate, propylene carbonate, diisopropyl sebacate and 1-dodecylazacycloheptan-2-one (See U.S. Pat. No. 3,989,816) (Sold under the tradename Azone, Nelson Research and Development Company, Irvine Calif.).

The solvents and carrying agents of the invention include such agents known in the art that are when incorporated into the vehicle and applied to the skin clear, colorless, volatile, non-malodorous and comfortable, that are dermatologically safe, and that are compatible with the active agents and other vehicle ingredients. The solvents and carrying agents can be used singly or in combination in concentration ranges suitable to bring the vehicle and active components up to the desired final strength. Solvents and carrying agents suitable for use in the present invention include, but are not limited to, ethyl alcohol, partially or fully deodorized alcohols and iso-alcohols, suitable denatured alcohols, methanol, water ketones, esters, ethers and the like. Advantageously, the alcohols are used at concentrations that are close to or below their minimal, antimicrobial inhibitory concentrations, because, at such concentrations, they possess better subjective qualities and minimal adverse skin acceptance problems, such as stinging. Thus, for example, concentrations of ethyl alcohol in the range of approximately 30% to 45% v/v are advantageous.

The drug delivery composition of that invention can also contain agents that chemically, physically and/or microbiocidally stabilize the active and other ingredients, agents that introduce aesthetically pleasing characteristics, and/or agents that protect the skin from ultra-violet and other radiation, free radicals and other internal and external insults. Such agents include preservatives, anti-oxidants, ultra-violet and radiation absorbing agents, free-radical inhibiting, quenching or neutralizing agents (for example tocopherol or derivatives thereof), colors, fragrances and the like. Effective concentrations of such agents are well known in the art or can readily be determined by one skilled in the art.

Active ingredients that can be included in the above-described delivery composition include, but are not limited to, retinoids, including trans and 13-cis retinoic acids, retinol, retinyl esters, and other physiologically active retinoid derivatives such as etretinate; steroidal, non-steroidal, retinoidal and other anti-inflammatories, such as hydrocortisone, dexamethasone, betamethasone and other steroids; non-steroidal antiinflammatories including ibuprofen and indomethacin; antibiotics such as erythromycin, ampicillin and clindamycin; antiviral agents such as acyclovir; agents such as antifungals, antimitotics, anesthetics, antihistamines, antibacterials, antipsoriatics, keratolytic, depigmenting and emollients; and agents that either stimulate, normalize or beneficially modify cellular formation and differentiation.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE I

The following is a specific example of three alternative formulations of the topical delivery composition of the present invention as described in general terms above.

| Formulation 1 | |
|---|---|
| Laureth-4 | 1.0% w/v |
| Glycerin | 2.0% w/v |
| Propylene Glycol | 2.0% w/v |
| Dimethylisosorbide | 0.5% w/v |
| Ethanol | 35.00% v/v |
| Preservatives | as needed |
| Water | to final volume |

| Formulation 2 | |
|---|---|
| Octoxynol-9 | 0.05% w/v |
| Glycerin | 2.40% w/v |
| Propylene Glycol | 0.60% w/v |
| Dioctyl Maleate | 1.00% w/v |
| Ethanol | 28.50% v/v |
| Preservatives | as needed |
| Water | to final volume |

| Formulation 3 | |
|---|---|
| Cocoamphocarboxyglycinate | 0.35% w/v |
| Caprylic/Capric Triglyceride | 0.25% w/v |
| Propylene Glycol | 2.00% w/v |
| Dimethylisosorbide | 1.00% w/v |
| Ethanol | 40.00% w/v |
| Pantothenol | 0.25% v/v |
| Preservatives | as needed |

| -continued | |
|---|---|
| UV A, B and other radiation screens | as needed |
| Free radical inhibitors or quenchers | as needed |
| Water | to final volume |

EXAMPLE II

The following is an example of a composition contemplated as one embodiment of the present invention containing a pharmaceutically acceptable retinoid sufficient to reverse the effects of aging upon the skin including wrinkling.

Formulation A contains 0.005% trans-retinoic acid whereas Formulation B contains 0.010% trans-retinoic acid and Formulation C contains 0.050% trans-retinoic acid.

| Formulation A 0.005% trans-retinoic acid | |
|---|---|
| Butylated hydroxytoluene | 0.015% |
| Disodium EDTA | 0.015% |
| Laureth-4 (Brij 30) | 1.00% |
| Glycerin | 2.00% |
| Propylene Glycol | 3.00% |
| 1-dodecylazacycloheptan-2-one | 0.10% |
| trans-retinoic acid | 0.00625% |
| | [0.005% + 20% excess] |
| SD-40 Ethanol, 95% v/v | 38.50% |
| Purified Water (distilled/deionized) | Q.S. |
| | [55.36375%] |

| Formulation B 0.010% trans-retinoic acid | |
|---|---|
| Butylated hydroxytoluene | 0.015% |
| Disodium EDTA | 0.015% |
| Laureth-4 (Brij 30) | 1.00% |
| Glycerin | 2.00% |
| Propylene Glycol | 3.00% |
| 1-dodecylazacycloheptan-2-one | 0.20% |
| trans-retinoic acid | 0.0120% |
| | [0.010% + 20% excess] |
| SD-40 Ethanol, 95% v/v | 43.50% |
| Purified Water (distilled/deionized) | Q.S. |
| | [50.258%] |

| Formulation C 0.050% trans-retinoic acid | |
|---|---|
| Butylated hydroxytoluene | 0.015% |
| Disodium EDTA | 0.015% |
| Laureth-4 (Brij 30) | 1.00% |
| Glycerin | 2.00% |
| Propylene Glycol | 3.00% |
| 1-dodecylazacycloheptan-2-one | 1.00% |
| trans-retinoic acid | 0.0625% |
| | [0.050% + 20% excess] |
| SD-40 Ethanol, 95% v/v | 48.50% |
| Purified Water (distilled/deionized) | Q.S. |
| | [44.4075%] |

EXAMPLE III

The following is an example of a composition contemplated as one embodiment of the present invention containing a pharmaceutically acceptable retinoid sufficient to reverse the effects of aging upon the skin such as wrinkling.

Formulation A contains 0.005% trans-retinoic acid whereas Formulation B contains 0.010% trans-retinoic acid and Formulation C contains 0.050% trans-retinoic acid.

| Formulation A 0.005% trans-retinoic acid | |
|---|---|
| Butylated hydroxytoluene | 0.015% |
| Disodium EDTA | 0.015% |
| Laureth-4 (Brij 30) | 1.00% |
| Glycerin | 2.00% |
| Propylene Glycol | 2.00% |
| Dimethylisosorbide | 0.50% |
| Alpha tocopherol | 0.01% |
| trans-retinoic acid | 0.00625% [0.005% + 20% excess] |
| SD-40 Ethanol, 95% v/v | 38.50% |
| Purified Water (distilled/deionized) | Q.S. [55.95375%] |

| Formulation B 0.010% trans-retinoic acid | |
|---|---|
| Butylated hydroxytoluene | 0.015% |
| Disodium EDTA | 0.015% |
| Laureth-4 (Brij 30) | 1.00% |
| Glycerin | 2.00% |
| Propylene Glycol | 2.00% |
| Dimethylisosorbide | 0.50% |
| Alpha tocopherol | 0.01% |
| trans-retinoic acid | 0.0120% [0.010% + 20% excess] |
| SD-40 Ethanol, 95% v/v | 38.50% |
| Purified Water (distilled/deionized) | Q.S. [55.948%] |

| Formulation C 0.050% trans-retinoic acid | |
|---|---|
| Butylated hydroxytoluene | 0.015% |
| Disodium EDTA | 0.015% |
| Laureth-4 (Brij 30) | 1.00% |
| Glycerin | 2.00% |
| Propylene Glycol | 2.00% |
| Dimethylisosorbide | 0.50% |
| Alpha tocopherol | 0.01% |
| trans-retinoic acid | 0.0625% [0.050% + 20% excess] |
| SD-40 Ethanol, 95% v/v | 38.50% |
| Purified Water (distilled/deionized) | Q.S. [55.8975%] |

EXAMPLE IV

The composition containing trans-retinoic acid as described in Formulation A in Example II above is compared to a prior art composition containing all trans-retinoic acid (See U.S. Pat. No. 3,906,108). The prior art composition described in that patent is as follows:

| Ingredient | grams |
|---|---|
| Tretinoin (All trans-retinoic acid) | 0.1 |
| Xanthan Gum, food grade | 0.3 |
| Polyoxy stearate, USP | 5.0 |
| Stearyl alcohol, USP | 3.0 |
| Stearic acid, USP | 19.0 |
| Isopropyl myristate, CTFA | 10.0 |
| Butylated hydroxytoluene | 0.1 |

-continued

| Ingredient | grams |
|---|---|
| Sorbic acid, NF | 0.2 |
| Purified Water, USP | q.s. to 100.0 ml |

The experiment is a double blind study. The test material is applied once each evening to the face for 12 months. Forty patients are enrolled into the study. Patients are assigned either the composition described as Formulation A in Example II above or the prior art composition described above.

After 6 months, the group using the composition described as Formulation A in Example II above shows a significantly lower drop out rate than does the group using the composition described in the prior art.

EXAMPLE V

An experiment is performed to demonstrate that the improved topical drug delivery composition of the present invention increases the efficacy of the pharmaceutically active ingredient tretinoin. Two formulations of the composition shown in Example II (containing 0.005% and 0.010% trans-retinoic acid) are compared to a prior art tretinoin gel composition. The ability of each vehicle to cause skin penetration of the active ingredient is analyzed.

The composition of the tretinoin gel is as follows: Approximately 0.010 to 0.025% tretinoin (trans-retinoic acid), approximately 1.0% hydroxypropyl cellulose, approximately 0.1% butylated hydroxytoluene, approximately 90% w/w Ethyl Alcohol and purified water.

When the skin penetration performance of the two formulations set forth in Example II (containing 0.005% and 0.010% trans-retinoic acid) are compared to that of the more potent tretinoin gel (containing 0.01% trans-retinoic acid), the penetration of each formulation set forth in Example II is greater by at least a factor of two than that of the 0.01% commercial tretinoin gel.

EXAMPLE VI

The effect of retinoids on the turnover time of the stratum cornium is assessed in vivo using the dansyl chloride method. The dansyl chloride method is known to those skilled in the art and is recognized as a measurement of biological activity. The biological activity of the embodiment of the composition of the present invention set forth above in Example II is compared with the prior art tretinoin gel composition described above in Example V.

The results show that the two formulations described in Example II (containing 0.005% and 0.010% trans-retinoic acid) induce an increase in regeneration time greater than that achieved by commercial tretinoin gel containing 0.01% trans-retinoic acid.

It should be understood, of course, that the foregoing relates only to a preferred embodiments of the present invention and that numerous modifications or alterations may be made therein without departing from the spirit and the scope of the invention as set forth in the appended claims.

We claim:

1. A topical composition consisting essentially of:
   i) laureth-4, present in about 1 percent by weight of the total composition;
   ii) propylene glycol, present in about 2 percent by weight of the total composition;

iii) dimethylsorbide, present in about 0.5 percent by weight of the total composition;

iv) trans-retinoic acid, present in about 0.01 percent by weight of the total composition; and v) a pharmaceutically acceptable diluent comprising a mixture of water and ethanol.

2. A method for transepithelial delivery of trans-retinoic acid to a human, comprising applying to the skin of the human a topical composition consisting essentially of i) laureth-4, present in about 1 percent by weight of the total composition;

ii) propylene glycol, present in about 2 percent by weight of the total composition;

iii) dimethylsorbide, present in about 0.5 percent by weight of the total composition;

iv) trans-retinoic acid, present in about 0.01 percent by weight of the total composition; and v) a pharmaceutically acceptable diluent comprising a mixture of water and ethanol.

3. A topical composition consisting essentially of:

i) laureth-4, present in about 1 percent by weight of the total composition;

ii) propylene glycol, present in about 2 percent by weight of the total composition;

iii) dimethylsorbide, present in about 0.5 percent by weight of the total composition;

iv) an effective amount of a pharmaceutically acceptable drug, wherein the drug is effective when administered topically; and v) a pharmaceutically acceptable diluent comprising a mixture of water and ethanol.

4. A method for transepithelial delivery of a drug to a human, comprising applying to the skin of the human a topical composition consisting essentially of:

i) laureth-4, present in about 1 percent by weight of the total composition;

ii) propylene glycol, present in about 2 percent by weight of the total composition;

iii) dimethylsorbide, present in about 0.5 percent by weight of the total composition;

iv) an effective amount of a pharmaceutically acceptable drug, wherein the drug is effective when administered topically; and v) a pharmaceutically acceptable diluent comprising a mixture of water and ethanol.

5. A topical composition consisting essentially of:

i) SDA-40 200 proof, present in about 36.8 percent by weight of the total composition;

i) butylated hydroxyanisole, present in about 0.15 percent by weight of the total composition;

ii) glycerin, present in about 2 percent by weight of the total composition;

iv) propylene glycol, present in about 2 percent by weight of the total composition;

v) purified distilled water, present in about 40 percent by weight of the total composition;

vi) pantethine, present in about 0.03 percent by weight of the total composition;

vii) laureth-4, present in about 1 percent by weight of the total composition;

viii) dimethylsorbide, present in about 0.5 percent by weight of the total composition;

ix) disodium EDTA, present in about 0.15 percent by weight of the total composition; and v) distilled water.

6. The composition of claim 5 further comprising a pharmaceutically active drug, wherein the drug is effective when administered topically.

7. The composition of claim 6 wherein that drug is trans-retinoic acid.

8. A method for transepithelial delivery of a drug to a human, comprising applying to the skin of the human a topical composition consisting essentially of:

i) SDA-40 200 proof present in about 36.8 percent by weight of the total composition;

ii) butylated hydroxyanisole, present in about 0.15 percent by weight of the total composition;

iii) glycerin USP 96 percent, present in about 2 percent by weight of the total composition;

iv) propylene glycol, present in about 2 percent by weight of the total composition;

v) purified distilled water, present in about 40 percent by weight of the total composition;

vi) pantethine 80 percent, present in about 0.03 percent by weight of the total composition;

vii) laureth-4, present in about I percent by weight of the total composition;

viii) dimethylsorbide, present in about 0.5 percent by weight of the total composition;

ix) disodium EDTA, present in about 0.15 percent by weight of the total composition;

x) a pharmaceutically active drug, wherein the drug is effective when administered topically; and xi) distilled water.

9. The composition of claim 8 wherein that drug is trans-retinoic acid.

* * * * *

UNITED STATES PATENT AND TRADEMARK OFFICE
CERTIFICATE OF CORRECTION

PATENT NO. : 6,028,105
DATED : February 22, 2000
INVENTOR(S) : Thomas P. Nigra and Eugene H. Gans It is certified that error appears in the above-indentified patent and that said Letters Patent is hereby corrected as shown below:

On title page, "Nigra" should read --Nigra et al--.

On title page, --Eugene H. Gans, 5 Fairview Drive, Westport, Connecticut 06880-- should be added as an inventor.

In Column 9, Line 52, "i" should read --ii--.

In Column 10, Line 1, "ii" should read --iii--.

In Column 10, Line 41, "I" should read --1--.

Signed and Sealed this

Fifteenth Day of May, 2001

Attest:

NICHOLAS P. GODICI

Attesting Officer     *Acting Director of the United States Patent and Trademark Office*